US012507875B2

(12) United States Patent
Saito

(10) Patent No.: US 12,507,875 B2
(45) Date of Patent: Dec. 30, 2025

(54) ENDOSCOPE AND ENDOSCOPE SYSTEM

(71) Applicant: OLYMPUS MEDICAL SYSTEMS CORP., Tokyo (JP)

(72) Inventor: Hidetoshi Saito, Hanno (JP)

(73) Assignee: Olympus Medical Systems Corp., Tokyo (JP)

( * ) Notice: Subject to any disclaimer, the term of this patent is extended or adjusted under 35 U.S.C. 154(b) by 424 days.

(21) Appl. No.: 18/079,913

(22) Filed: Dec. 13, 2022

(65) Prior Publication Data

US 2023/0190082 A1 Jun. 22, 2023

Related U.S. Application Data

(60) Provisional application No. 63/291,122, filed on Dec. 17, 2021.

(51) Int. Cl.
*A61B 1/00* (2006.01)
*A61B 1/018* (2006.01)

(52) U.S. Cl.
CPC .......... *A61B 1/018* (2013.01); *A61B 1/00096* (2013.01); *A61B 1/00098* (2013.01)

(58) Field of Classification Search
CPC . A61B 1/018; A61B 1/00096; A61B 1/00098; A61B 1/126
USPC .................................. 600/104, 107; 604/264
See application file for complete search history.

(56) References Cited

U.S. PATENT DOCUMENTS

| | | | | | |
|---|---|---|---|---|---|
| 4,793,326 | A * | 12/1988 | Shishido | A61B 1/018 | 600/114 |
| 6,579,270 | B2 * | 6/2003 | Sussman | A61F 9/00736 | 604/27 |
| 2002/0091303 | A1 * | 7/2002 | Ootawara | A61B 1/01 | 600/106 |
| 2006/0281973 | A1 * | 12/2006 | Sugita | A61B 1/0008 | 600/156 |
| 2008/0154091 | A1 * | 6/2008 | Dejima | A61B 17/29 | 600/104 |
| 2014/0276908 | A1 * | 9/2014 | Raybin | A61B 18/149 | 606/113 |
| 2017/0182520 | A1 * | 6/2017 | Yamaya | G02B 23/2476 | |
| 2017/0215704 | A1 * | 8/2017 | Tsumaru | A61B 1/00128 | |

(Continued)

FOREIGN PATENT DOCUMENTS

| | | |
|---|---|---|
| JP | H07-194525 A | 8/1995 |
| JP | H08-173376 A | 7/1996 |

(Continued)

*Primary Examiner* — Anh Tuan T Nguyen
*Assistant Examiner* — James Edward Boice
(74) *Attorney, Agent, or Firm* — Morgan, Lewis & Bockius LLP

(57) ABSTRACT

An endoscope comprises an insertion portion including a distal end portion having a longitudinal axis. The distal end portion includes an inner surface forming a recess, a first channel extending in a first direction and configured to receive a treatment instrument, the first channel including a first opening disposed at the inner surface of the recess, a raising base disposed in the recess and configured to direct a distal end of the treatment instrument received in the first channel, and a second channel including a second opening disposed at the inner surface, the second channel configured to discharge a first liquid to inside of the recess via the second opening.

19 Claims, 7 Drawing Sheets

(56) References Cited

U.S. PATENT DOCUMENTS

| | | | | |
|---|---|---|---|---|
| 2018/0078121 | A1* | 3/2018 | Yasuda | A61B 1/00177 |
| 2018/0235453 | A1* | 8/2018 | Morimoto | A61B 1/126 |
| 2021/0127965 | A1* | 5/2021 | Yamaya | A61B 1/126 |
| 2021/0161361 | A1* | 6/2021 | Flanagan | A61B 1/0057 |
| 2021/0315446 | A1* | 10/2021 | Crawford | A61B 1/00177 |
| 2021/0361145 | A1* | 11/2021 | Harada | A61B 1/00098 |

FOREIGN PATENT DOCUMENTS

| | | | |
|---|---|---|---|
| JP | H10-262910 | A | 10/1998 |
| JP | 2001-000389 | A | 1/2001 |
| JP | 2002-085347 | A | 3/2002 |
| JP | 3300146 | B2 | 7/2002 |
| JP | 3509244 | B2 | 3/2004 |
| JP | 2015-029764 | A | 2/2015 |

* cited by examiner

ENDOSCOPE AND ENDOSCOPE SYSTEM

RELATED APPLICATION DATA

This application is based on and claims priority under 35 U.S.C. § 119 to U.S. Provisional Application No. 63/291,122 filed on Dec. 17, 2021, the entire contents of which are incorporated herein by reference.

FIELD OF THE DISCLOSURE

The present disclosure relates to an endoscope in which a treatment instrument passes through an insertion portion, and an endoscope system including the endoscope in which the treatment instrument passes through the insertion portion.

BACKGROUND

Sterilization and cleaning work (reprocess) is performed after an endoscope is used to prevent contamination by bacteria when the endoscope is reused. A single-use, in other words, disposable endoscope is sealed in a package in a sterile condition and is taken out from the package immediately before use.

Japanese Patent Application Laid-Open Publication No. H10-262910 discloses an endoscope in which a tube is sterilized by filling the tube with a transparent liquid for ultraviolet propagation and irradiating the tube with ultraviolet from an end portion.

Japanese Patent Application Laid-Open Publication No. 2002-85347 discloses an endoscope system in which a fluid flowing through a tube is sterilized with a bactericidal lamp.

Japanese Patent Application Laid-Open Publication No. H8-173376 discloses an endoscope in which an image pickup unit including an image pickup window is disposed at a distal end portion, and a cleaning water is discharged toward the image pickup window.

Japanese Patent Application Laid-Open Publication No. 2015-29764 discloses an endoscope in which water is fed from a distal end of an insertion portion to an observation range to clean and color a target site.

SUMMARY OF THE DISCLOSURE

An endoscope comprises an insertion portion including a distal end portion having a longitudinal axis. The distal end portion includes an inner surface forming a recess, a first channel extending in a first direction and configured to receive a treatment instrument, the first channel including a first opening disposed at the inner surface of the recess, a raising base disposed in the recess and configured to direct a distal end of the treatment instrument received in the first channel, and a second channel including a second opening disposed at the inner surface, the second channel configured to discharge a first liquid to inside of the recess via the second opening.

DETAILED DESCRIPTION

First Embodiment

Figure 1:
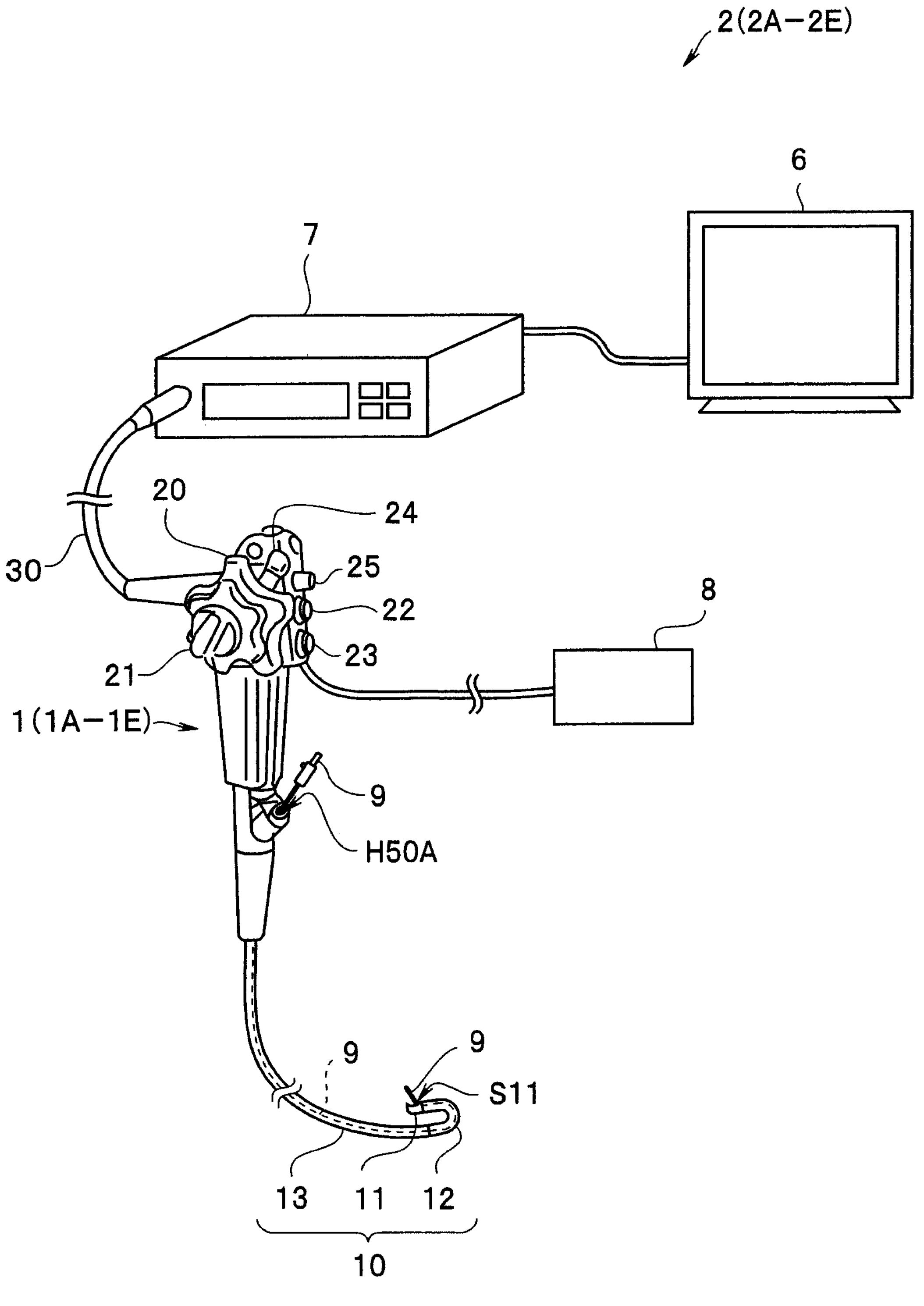
FIG. 1 is a perspective view of an endoscope system of an embodiment.

An endoscope 1 of the present embodiment illustrated in FIG. 1 constitutes an endoscope system 2 with a treatment instrument 9, a monitor 6, a processor 7 and a liquid feed device 8. The endoscope 1 is, for example, a side-view duodenoscope to be used in treatment of collecting gallstones in a common bile duct using the treatment instrument 9.

Note that the drawings based on the embodiment are schematic drawings. A relationship between a thickness and a width of each portion, a ratio of thicknesses of respective portions, or the like, in the drawings are different from an actual relationship, ratio, or the like. Parts where a relationship of dimensions and ratios are different between the drawings are included. Illustration and assignment of reference numerals of part of components will be omitted.

The endoscope 1 includes an insertion portion 10 to be inserted into a subject, an operation portion 20 provided on a proximal end side of the insertion portion 10, and a universal cord 30 extending from the operation portion 20.

The insertion portion 10 includes a distal end portion 11 disposed at a distal end, a bending portion 12 disposed on a proximal end side of the distal end portion 11, and a flexible tube 13 that connects a proximal end side of the bending portion 12 and the operation portion 20, which are continuously provided. The distal end portion 11 of the insertion portion 10 has a longitudinal axis. The distal end portion includes an inner surface forming a recess S11, a treatment instrument channel 50 extending in a first direction and configured to receive a treatment instrument 9, the treatment instrument channel 50 including a first opening disposed at the inner surface of the recess S11, a raising base 55 disposed in the recess S11 and configured to direct a distal end of the treatment instrument 9 received in the treatment instrument channel 50, and a first liquid feed channel 61 including a first cleaning nozzle (opening) H61 disposed at the inner surface, the first liquid feed channel 61 configured to discharge a first liquid to inside of the recess S11 via the first cleaning nozzle H61. The first liquid is discharged toward the raising base 55. A discharge area of the first liquid covers an outer diameter of the treatment instrument 9 disposed at the raising base 12A.

At the operation portion 20, a bending operation dial 21, an air/water feeding button 22, a suction button 23, a raising base operation lever 24, and a plurality of operation switches 25 are provided. The bending portion 12 bends in accordance with rotation of the bending operation dial 21. The operation switches 25 are electronic switches that operate an image pickup unit 40 (FIG. 2), and the like.

At the operation portion 20, an insertion port H50A for introducing the treatment instrument 9 into the insertion portion 10 is provided. A proximal end side of a treatment instrument channel 50 (FIG. 3) is connected to the insertion port H50A. A recess S11 at the distal end portion 11 of the insertion portion 10 communicates with the treatment instrument channel 50. An inner surface forming the recess S11 includes a proximal surface, a distal surface, and a plurality of side surfaces connecting the proximal surface to the distal surface, and wherein the first opening of the treatment instrument channel 50 is in the proximal surface.

A raising base operation wire 12A (FIG. 5) passes through the insertion portion 10. The raising base operation wire 12A moves forward and backward in accordance with operation of the raising base operation lever 24.

The processor 7 including a CPU processes an image pickup signal outputted by an image pickup unit 40 and transmits an image signal to the monitor 6. The monitor 6 displays an endoscope image. The processor 7 includes a light source circuit that generates illumination light, and the like, which will be described later. The light source circuit may be incorporated into a light source unit different from the processor 7.

The treatment instrument 9 is inserted into the treatment instrument channel 50 from the insertion port H50A of the endoscope 1, and a distal end of the treatment instrument 9 projects from the recess S11.

The liquid feed device 8 supplies a liquid for cleaning to the endoscope 1.

Configuration of Distal End Portion

Figure 2:
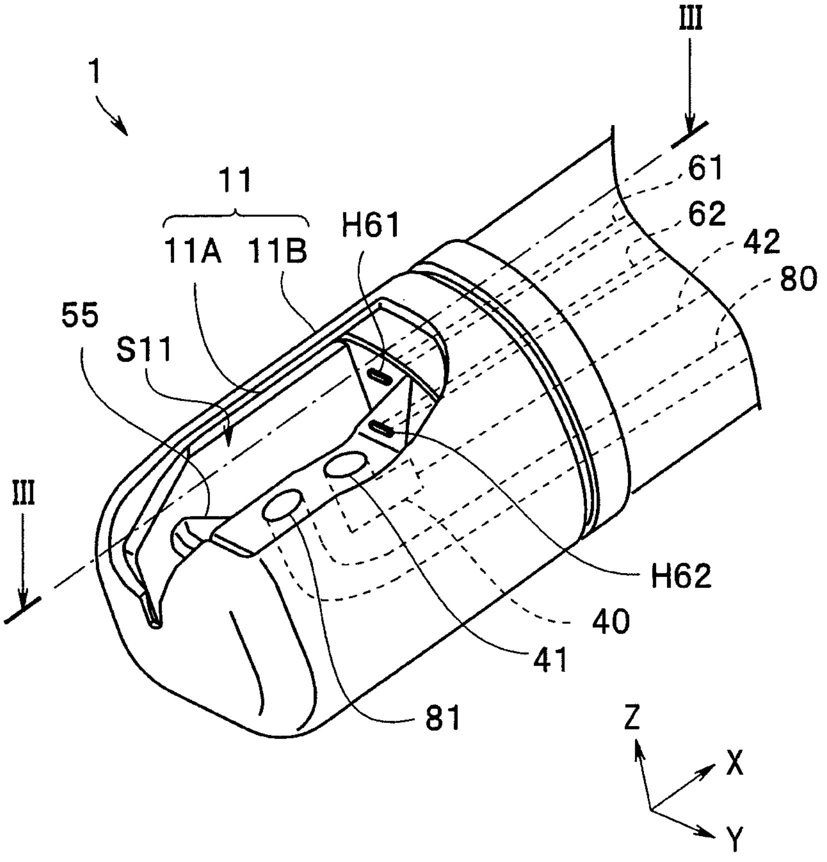
FIG. 2 is a perspective view of a distal end portion of an endoscope of a first embodiment.
Figure 3:
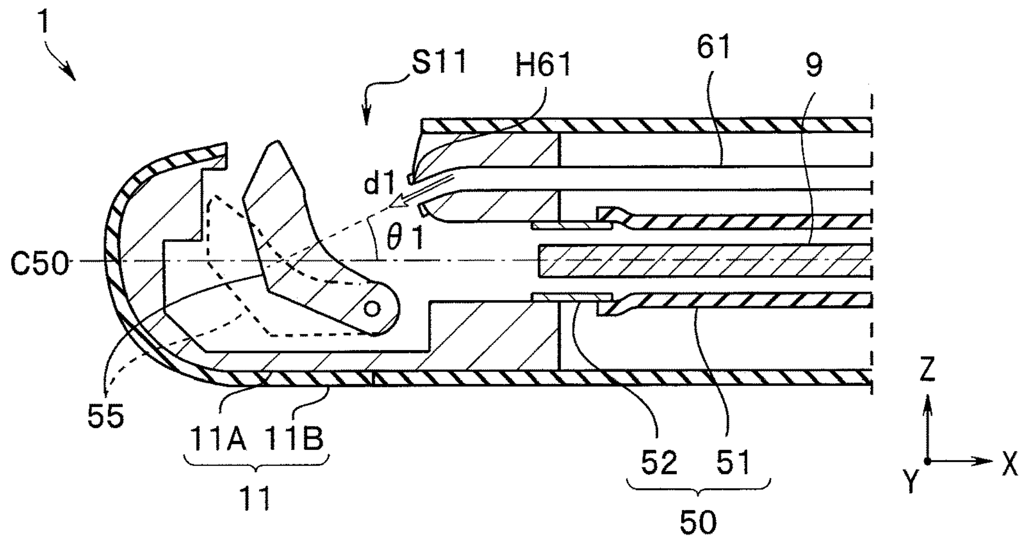
FIG. 3 is a cross-sectional view along a line in FIG. 2.
Figure 4:
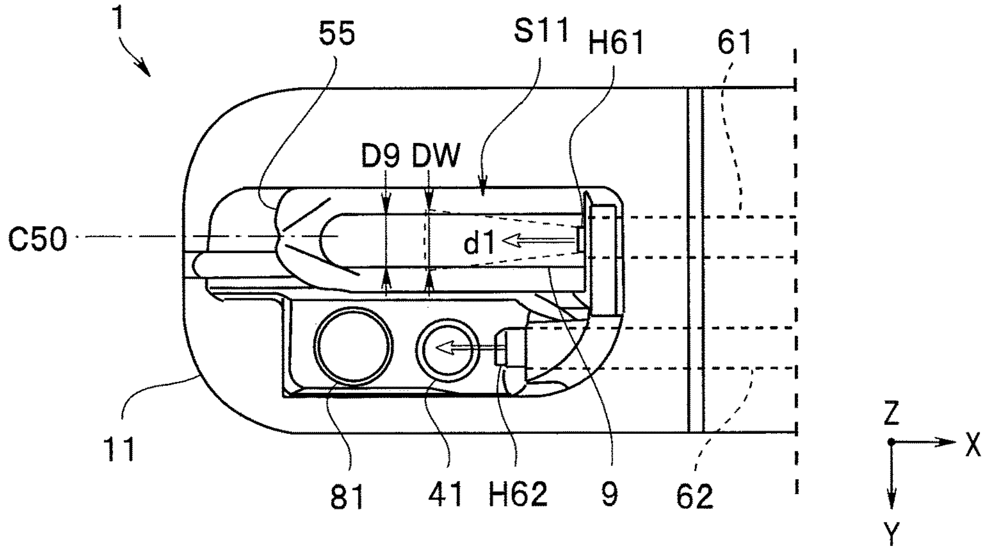
FIG. 4 is a top view of the distal end portion of the endoscope of the first embodiment.

FIG. 3 is a cross-sectional view along a line in FIG. 2. FIG. 3 illustrates a first plane (XZ plane) including the treatment instrument channel 50 and a first liquid feed channel 61. FIG. 4 is a top view of the distal end portion 11 and illustrates a second plane (XY plane) perpendicular to the first plane.

A distal end constituent member 11A that is a main member of the distal end portion 11 of the endoscope 1 is a rigid member formed with a metal or a resin. The distal end constituent member 11A is partially covered with a distal end cover 11B. The distal end constituent member 11A includes the recess S11 in which a treatment instrument raising base 55 (hereinafter, referred to as a "raising base") is accommodated. The recess S11 is a space between a pair of arm portions of the distal end constituent member 11A, projecting toward the distal end side.

The raising base 55 is a tongue-shaped member. The treatment instrument 9 such as a forceps is configured to be inserted into the treatment instrument channel 50 (51, 52) from the insertion portion H50A, pass through the treatment instrument channel 50 and project from the recess S11.

A projecting direction of the treatment instrument 9 projecting from the recess S11 is operated by the raising base 55. The raising base 55 is connected to a distal end of the raising base operation wire 12A. A state of the raising base 55 becomes an upright state from a laid state by the raising base 55 rotating in accordance with a backward movement of the raising base operation wire 12A. A projecting direction (projecting angle) of the treatment instrument 9 changes in accordance with an upright angle of the raising base 55. The treatment instrument 9 is translatable in the treatment instrument channel 50 to project from the opening in a projecting direction, and the raising base 55 is operable to change the projecting direction of the treatment instrument 9.

The treatment instrument channel 50 includes a channel pipe 52 and a channel tube 51 which is continuously provided with the channel pipe 52 and which is formed with a flexible fluorine resin, or the like. The channel pipe 52 is disposed at an opening on a proximal end side of a through-hole of the distal end constituent member 11A. The channel pipe 52 is formed with a metal such as stainless steel.

A first cleaning nozzle H61 that is a first discharge outlet (first opening) is disposed on a wall surface on a proximal end side of the recess S11. The first cleaning nozzle H61 is open toward inside of the recess S11. A liquid (for example, a normal saline solution or sterilized water) fed from the liquid feed device 8 is discharged from the first cleaning nozzle H61 that is a discharge outlet projecting port of the first liquid feed channel 61, toward inside of the recess S11.

As illustrated in FIG. 3, on the first plane (XZ plane) including the treatment instrument channel 50 and the first liquid feed channel 61, the first cleaning nozzle H61 is open in a first direction d1 that intersects a longitudinal axis C50 of a distal end portion (channel pipe 52) of the treatment instrument channel 50 at an acute angle θ1, and a liquid is discharged in the first direction d1. The first liquid feed channel 61 includes a bent portion located at a distal end of the first liquid feed channel 61, wherein the bent portion extends in the first direction d1, and the first direction d1 intersects the direction of the treatment instrument channel 50 at an acute angle θ1. The bent portion includes the second opening.

Before the treatment instrument 9 is inserted into the endoscope 1, the raising base 55 is in a laid state. The liquid discharged in the first direction d1 can clean the raising base 55 in the laid state.

Note that as illustrated in FIG. 4, on the second plane (XY plane) perpendicular to the first plane (XZ plane), the longitudinal axis C50 of the treatment instrument channel 50 is substantially parallel to the first direction d1.

The liquid is discharged at a width Dw wider than an outer diameter S9 of the treatment instrument 9 at a position of the treatment instrument 9 disposed at the recess S11 and cleans an outer surface of the treatment instrument 9.

Note that an illumination window 81, an image pickup window 41 of the image pickup unit 40 and a second cleaning nozzle H62 are disposed on an upper surface of the distal end constituent member 11A. An illumination optical system including the illumination window 81 emits light guided by an optical fiber 80 toward the subject. The image pickup unit 40 receives light of a subject image. The image pickup unit 40 is driven with power received from the processor 7 by way of a cable 42. The image pickup unit 40 converts the light of the subject image collected by an optical system including the image pickup window into an image pickup signal by an image pickup device such as a CCD and transmits the image pickup signal to the processor 7 by way of the cable 42.

The second cleaning nozzle H62 is a discharge outlet (second opening) of a second liquid feed channel 62. The second cleaning nozzle H62, which is open toward the image pickup window 41, discharges a liquid (for example, water) fed from the liquid feed device 8 to the illumination window 81 and the image pickup window 41. The distal end portion 11 includes the image pickup window 41, and the second liquid feed channel 62 including the second cleaning nozzle (an opening) H62 disposed outside of the recess S11, wherein the second liquid feed channel 62 is configured to discharge a second liquid toward the image pickup window 41 via the second cleaning nozzle H62. The first liquid and the second liquid are supplied from a common reservoir. The second cleaning nozzle H62 is in one of the plurality of side surfaces and the second cleaning nozzle H62 is configured to discharge a second liquid toward the image pickup window via the third opening.

Figure 5:
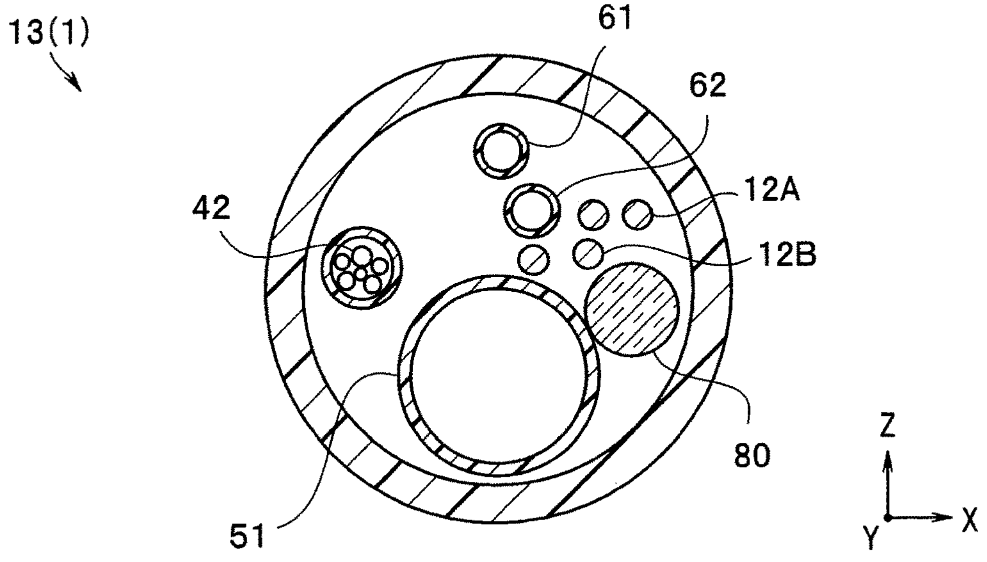
FIG. 5 is a cross-sectional view of a flexible tube of the endoscope of the first embodiment.

Note that as illustrated in FIG. 5, the raising base operation wire 12A, a bending operation wire 12B, the cable 42, the channel tube 51, the first liquid feed channel 61, the second liquid feed channel 62 and the optical fiber 80 pass through the flexible tube 13 of the insertion portion 10.

The first liquid feed channel 61 and the second liquid feed channel 62 may be merged on a proximal end side to constitute one liquid feed tube. The flexible tube 13 of an endoscope in which one liquid feed channel includes two discharge outlet is thin.

The endoscope 1 is a single-use endoscope. There is no possibility that the single-use endoscope 1 is contaminated with bacteria before a sterile package is open. However, there is a case where environmental bacteria or bacteria in the body of a patient are attached after the endoscope 1 is taken out from the sterile package. Further, even if the treatment instrument 9 is a single-use treatment instrument, there is also a case where bacteria are attached after the treatment instrument 9 is taken out from a sterile package.

For example, there is a possibility that resident microbiota of the oral cavity of a subject or environmental bacteria are attached to an inner surface of the recess S11 of the distal end portion 11 inserted into duodenum by way of the oral cavity of the subject, and a member such as the raising base 55 accommodated in the recess S11. At the endoscope 1, the bacteria attached to the recess S11 can be cleaned with a liquid discharged from the first cleaning nozzle H61. Note that bacteria attached to the treatment instrument 9 disposed at the recess S11 can also be cleaned with the liquid discharged from the first cleaning nozzle H61 immediately before the treatment instrument 9 is inserted into a biliary tract.

According to the endoscope 1 and the endoscope system 2, bacteria attached to the raising base 55 can be cleaned after the endoscope 1 is taken out from the sterile package. Further, according to the endoscope 1 and the endoscope system 2, cleaning can be performed before the treatment instrument 9 that is to pass through the channel 50 is inserted into a biliary tract in a sterile condition.

Modifications of the embodiment and other embodiments will be described below.

The modifications and other embodiments are similar to the endoscope 1 and the endoscope system 2 in the first embodiment and provide the same effects. Thus, in the following description, the same reference numerals will be assigned to components having functions that are the same as the functions of the endoscope 1 and the endoscope system 2 in the first embodiment, and description will be omitted.

Modification 1 of First Embodiment

Figure 6:
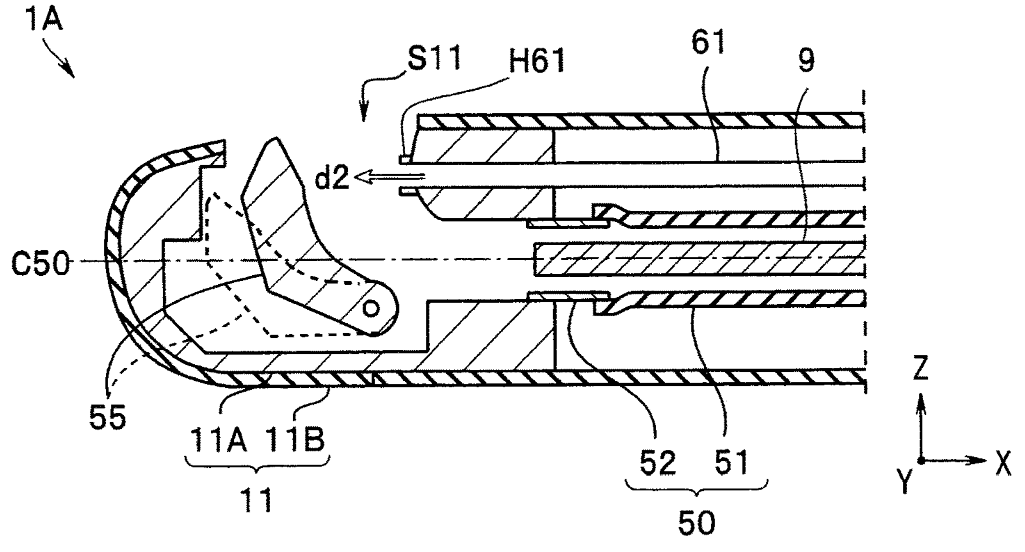
FIG. 6 is a cross-sectional view of a distal end portion of an endoscope in modification 1 of the first embodiment.

As illustrated in FIG. 6, in an endoscope 1A of the present modification, on the first plane (XZ plane) including the treatment instrument channel 50 and the first liquid feed channel 61, the first cleaning nozzle H61 that is the first discharge outlet is open in a second direction d2 parallel to the longitudinal axis C50 of the treatment instrument channel 50, and a liquid is discharged in the second direction d2.

In other words, an opening direction of the first cleaning nozzle H61 does not have to intersect the longitudinal axis C50 of the treatment instrument channel 50 on the first plane (XZ plane) if inside of the recess S11 can be cleaned. The first liquid feed channel 61 extends in a second direction d2, and the second direction is parallel to the first direction. Here, parallel includes a range where design errors are included and a range of effects and functions similar to those of this disclosure.

Modification 2 of First Embodiment

Figure 7:
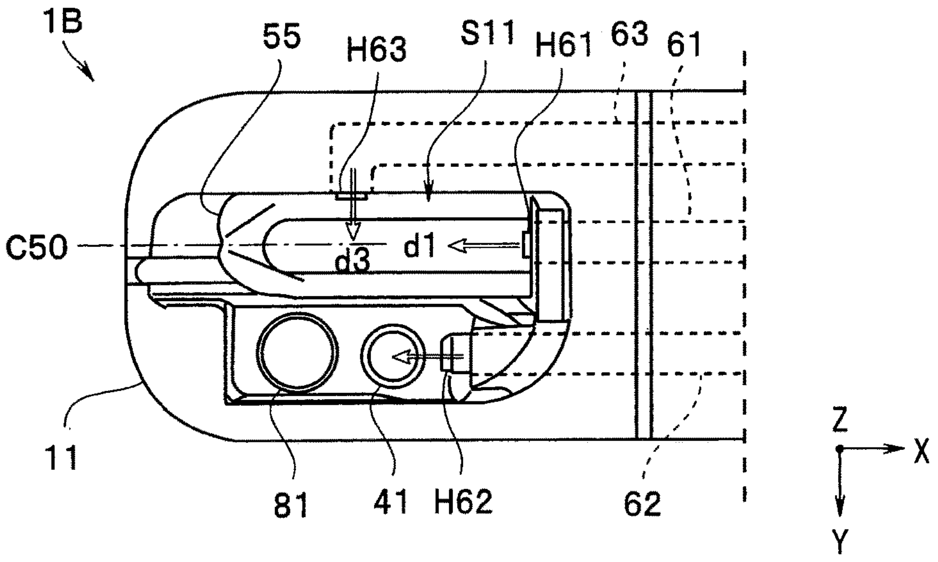
FIG. 7 is a top view of a distal end portion of an endoscope of modification 2 of the first embodiment.

As illustrated in FIG. 7, an endoscope 1B of the present modification includes a third liquid feed channel 63 in addition to the first liquid feed channel 61 and the second liquid feed channel 62.

Figure 8:
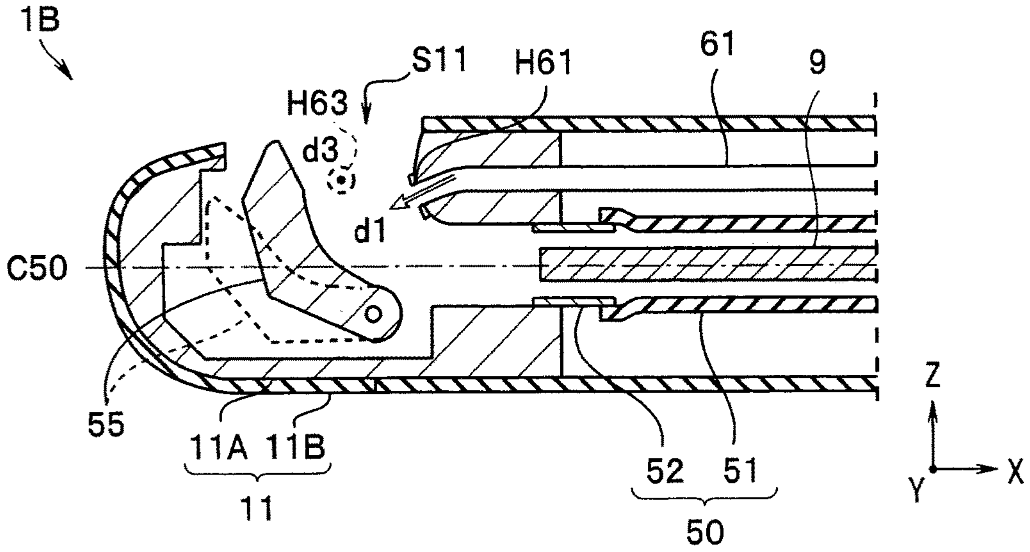
FIG. 8 is a cross-sectional view of the distal end portion of the endoscope of modification 2 of the first embodiment.

A third cleaning nozzle H63 that is a discharge outlet (third opening) of the third liquid feed channel 63 is located on a wall surface on a side surface side of the recess S11. The third cleaning nozzle H63 that is a third discharge outlet is open in a third direction d3 that is orthogonal to the longitudinal axis C50 of the treatment instrument channel 50 on the second plane (XY plane) perpendicular to the first plane (XZ plane). Note that as illustrated in FIG. 8, the third direction d3 is a direction perpendicular to the paper of FIG. 8. The first direction d1 does not intersect the third direction d3. The third liquid feed channel 63 includes the third cleaning nozzle (opening) H63, wherein the third cleaning nozzle H63 is in one of the plurality of side surfaces of the recess S11.

In the endoscope 1B, a liquid is discharged in two directions d1 and d3. Thus, according to the endoscope 1B, it is possible to more reliably clean inside of the recess S11 and the treatment instrument 9 than the endoscope 1.

The first liquid feed channel 61, the second liquid feed channel 62 and the third liquid feed channel 63 may be merged on a proximal end side to constitute one liquid feed channel.

Modification 3 of First Embodiment

Figure 9:
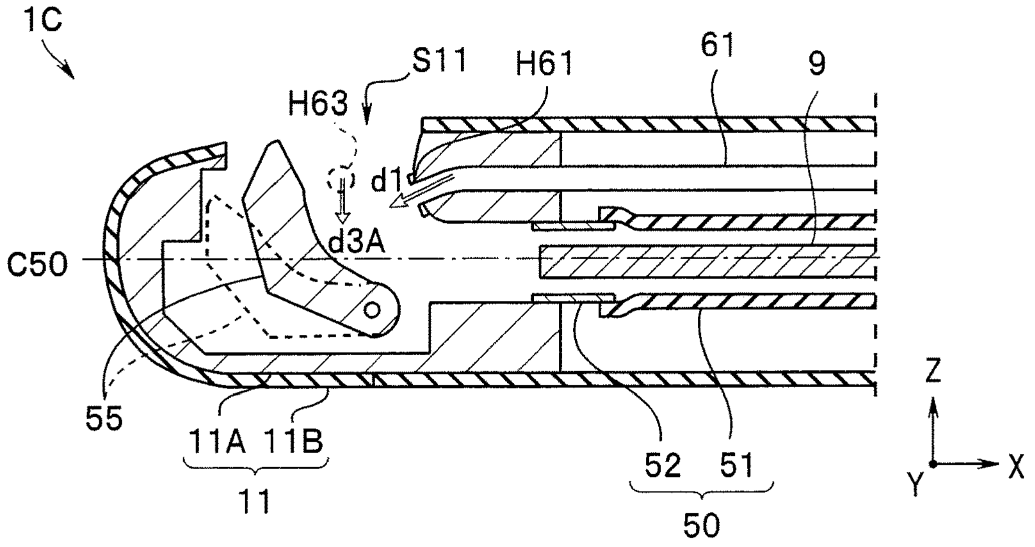
FIG. 9 is a cross-sectional view of a distal end portion of an endoscope of modification 3 of the first embodiment.

As illustrated in FIG. 9, in an endoscope 1C of the present modification, an opening direction d3A of the third cleaning nozzle H63 of the third liquid feed channel 63 intersects an opening direction d1 of the first cleaning nozzle H61 inside the recess S11. The recess S11 further includes a bottom surface, and the opening direction d3A intersects the bottom surface of the recess S11.

In the endoscope 1C, a liquid discharged from the first cleaning nozzle H61 intersects a liquid discharged from the third cleaning nozzle H63 inside the recess S11. A region where the liquids intersect is set in, for example, a region where the treatment instrument 9 contacts the raising base 55.

According to the endoscope 1C, it is possible to more reliably clean bacteria attached to the treatment instrument 9 than the endoscope 1B.

Modification 4 of First Embodiment

Figure 10:
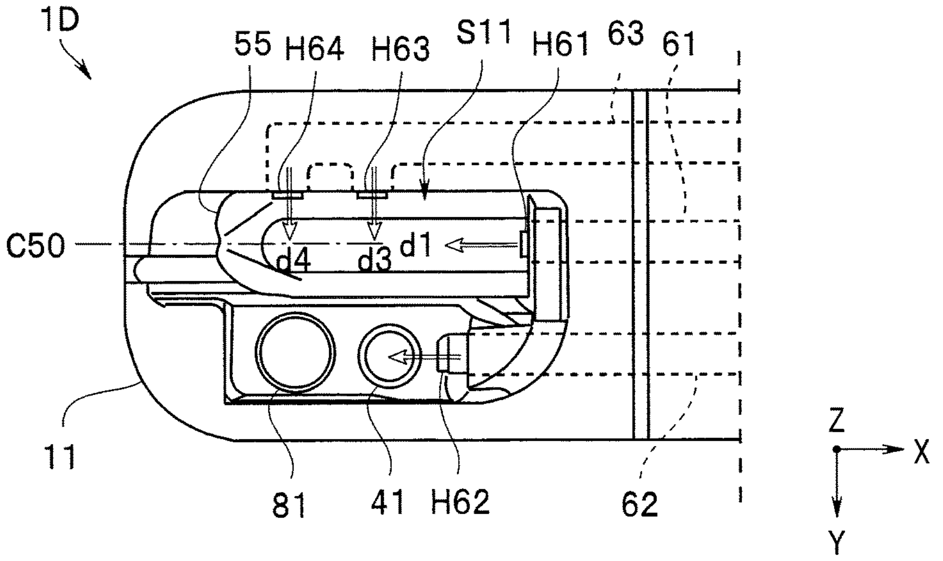
FIG. 10 is a top view of a distal end portion of an endoscope of modification 4 of the first embodiment.

As illustrated in FIG. 10, in an endoscope 1D of the present modification, the third liquid feed channel 63 includes two discharge outlets. The third cleaning nozzle H63 and a fourth cleaning nozzle H64 that are discharge outlets of the third liquid feed channel 63 are both open in the third direction d3 and a fourth direction d4 that are orthogonal to the longitudinal axis C50 of the treatment instrument channel 50 on the second plane (XY plane). The third cleaning nozzle H63 and the fourth cleaning nozzle H64 are in one of the plurality of side surfaces of the recess S11.

The endoscope 1D may include a fourth liquid feed channel including the fourth cleaning nozzle H64 in addition to the third liquid feed channel 63 including the third cleaning nozzle H63. The first liquid is discharged from the third liquid feed channel 63 via the third cleaning nozzle H63 is a first liquid portion, the third liquid feed channel 63 further includes a fourth cleaning nozzle H64 disposed at the inner surface, and the third liquid feed channel 63 is configured to discharge a second liquid portion to inside of the recess S11 via the fourth cleaning nozzle H64. The first liquid portion is directed toward the raising base 55 and the second liquid portion is directed toward the raising base 55. The first liquid portion is directed toward a first portion of the raising base 55 and the second liquid portion is directed toward a second portion of the raising base 55, where the first portion of the raising base 55 is different from the second portion of the raising base 55.

According to the endoscope 1D, it is possible to more reliably clean inside of the recess S11 and the treatment instrument 9 than the endoscope 1, and the like.

Second Embodiment

Figure 11:
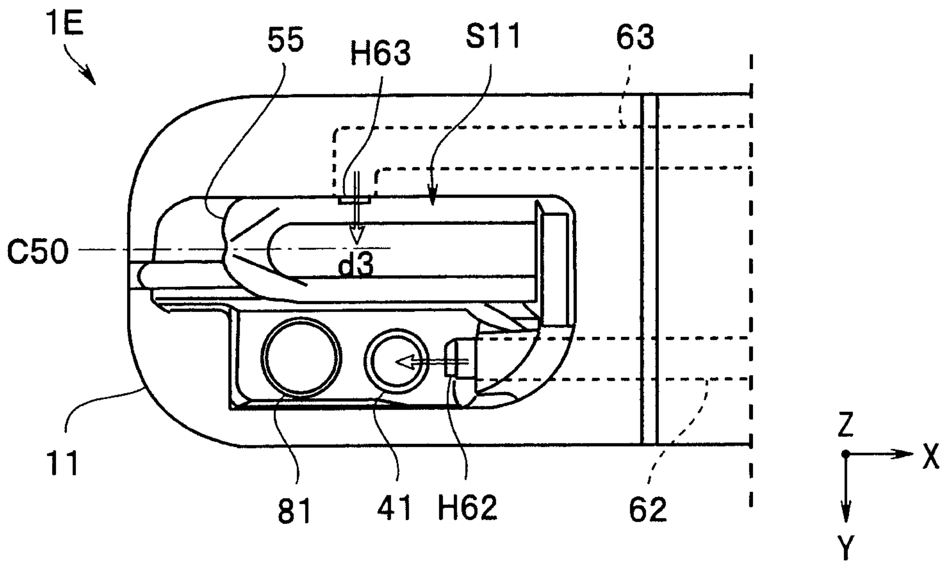
FIG. 11 is a top view of a distal end portion of an endoscope of a second embodiment.

As illustrated in FIG. 11, an endoscope 1E of a second embodiment includes only the third cleaning nozzle H63 that is open in the third direction d3 orthogonal to the longitudinal axis C50 of the treatment instrument channel 50 on the second plane (XY plane). In the endoscope 1E, the third cleaning nozzle H63 is the first discharge outlet, and the liquid feed channel 63 is the first liquid feed channel. A liquid is discharged in the third direction d3. The third cleaning nozzle H63 is in one of the plurality of side surfaces of the recess S11.

The third liquid feed channel 63 of the endoscope may include a fourth cleaning nozzle H64 that discharges a liquid in the fourth direction d4. Further, the third liquid feed channel 63 of the endoscope may include the third cleaning nozzle H63 and the fourth cleaning nozzle H64. The fourth cleaning nozzle H64 is in one of the plurality of side surfaces of the recess S11.

While the endoscope 1, and the like, are flexible endoscopes, endoscopes of other embodiments may be rigid endoscopes including rigid straight tubes.

It goes without saying that endoscope systems 2A to 2E including the endoscopes 1A to 1E provide effects that are the same as the effects of the endoscope system 2 and effects of the endoscopes 1A to 1E.

The present disclosure is not limited to the embodiment explained above. Various changes, alterations, and the like are possible within a range not changing the gist of the disclosure.

Example 1. An endoscope comprising:
- an insertion portion including a distal end portion including a recess at which a raising base is disposed, the insertion portion being configured to be inserted into a subject;
- a treatment instrument channel disposed at the insertion portion, a treatment instrument passing through the treatment instrument channel and being configured to project from the recess, a projecting direction of the treatment instrument being operated by the raising base; and
- a first liquid feed tube including a first discharge outlet disposed on a wall surface of the recess, the first discharge outlet being open toward inside of the recess and configured to discharge a liquid to the inside of the recess.

Example 2. The endoscope according to Example 1, wherein
- an image pickup unit including an image pickup window is disposed at the distal end portion, and
- the endoscope further comprises
- a second liquid feed tube including a second discharge outlet open toward the image pickup window and configured to discharge the liquid toward the image pickup window.

Example 3. The endoscope according to Example 2, wherein
- on a first plane including the treatment instrument channel and the first liquid feed tube, the first discharge outlet is open in a first direction intersecting a longitudinal axis of a distal end portion of the treatment instrument channel, and the liquid is discharged in the first direction.

Example 4. The endoscope according to Example 2, wherein
- on a first plane including the treatment instrument channel and the first liquid feed tube, the first discharge outlet is open in a first direction intersecting a longitudinal axis of a distal end portion of the treatment instrument channel at an acute angle, and the liquid is discharged in the first direction.

Example 5. The endoscope according to Example 2, wherein
- on a first plane including the treatment instrument channel and the first liquid feed tube, the first discharge outlet is open in a second direction parallel to a longitudinal axis of a distal end portion of the treatment instrument channel, and the liquid is discharged in the second direction.

Example 6. The endoscope according to Example 4, further comprising
- a third liquid feed tube including a third discharge outlet open in a third direction orthogonal to the longitudinal axis of the distal end portion of the treatment instrument channel on a second plane perpendicular to the first plane, wherein
- the liquid is discharged in the third direction.

Example 7. The endoscope according to Example 2, wherein
- the liquid is discharged at a width wider than an outer diameter of the treatment instrument at a position of the treatment instrument disposed at the recess and cleans an outer surface of the treatment instrument.

Example 8. The endoscope according to Example 2, wherein
- the liquid is discharged in a plurality of directions.

Example 9. The endoscope according to Example 2, wherein
- the liquid is discharged in two directions, and the two directions intersect on a first plane including the treatment instrument channel and the first liquid feed tube.

Example 10. The endoscope according to Example 9, wherein
- the liquid intersects inside the recess.

Example 11. The endoscope according to Example 2, wherein
- on a second plane perpendicular to a first plane including the treatment instrument channel and the first liquid feed tube, the first discharge outlet is open in a third direction orthogonal to the second plane, and the liquid is discharged in the third direction.

Example 12. An endoscope system comprising:
- an endoscope comprising an insertion portion including a distal end portion including a recess at which a raising base is disposed, the insertion portion being configured to be inserted into a subject, a treatment instrument channel disposed at the insertion portion, and a first liquid feed tube including a first discharge outlet disposed on a wall surface of the recess, the first discharge outlet being open toward inside of the recess and configured to discharge a liquid to the inside of the recess;

a liquid feed device configured to supply the liquid to the first liquid feed tube; and a treatment instrument passing through the treatment instrument channel and being configured to project from the recess, a projecting direction of the treatment instrument being operated by the raising base.

Example 13. The endoscope system according to Example 12, wherein an image pickup unit including an image pickup window is disposed at the distal end portion, and the endoscope system further comprises a second liquid feed tube including a second discharge outlet configured to discharge the liquid toward the image pickup window.

Example 14. The endoscope system according to Example 13, wherein on a first plane including the treatment instrument channel and the first liquid feed tube, the first discharge outlet is open in a first direction intersecting a longitudinal axis of a distal end portion of the treatment instrument channel at an acute angle, and the liquid is discharged in the first direction.

Example 15. The endoscope system according to Example 14, further comprising a third discharge outlet open in a third direction orthogonal to the longitudinal axis on a second plane perpendicular to the first plane, wherein the liquid is discharged in the third direction.

What is claimed is:

1. An endoscope, comprising:

an insertion portion including a distal end portion having a longitudinal axis, the distal end portion including:

an inner surface forming a recess, a first channel extending in a first direction and configured to receive a treatment instrument, the first channel including a first opening disposed at the inner surface of the recess, a raising base disposed in the recess and configured to direct a distal end of the treatment instrument received in the first channel, and a second channel extending within the insertion portion and including a second opening contained in a nozzle disposed at a distal end of the second channel, wherein the nozzle includes a second opening disposed at the inner surface of the recess, wherein the second channel includes a bent part located between a distal portion of the second channel and a proximal portion of the second channel, wherein the distal portion of the second channel extends along a discharge axis from the bent part to the second opening included in the nozzle, wherein the second channel is configured to discharge a first liquid in a discharge direction along the discharge axis to an inside of the recess via the second opening included in the nozzle, wherein the discharge axis intersects the raising base, and wherein, in the discharge direction of the discharge axis, the discharge axis intersects the first direction at an acute angle.

2. The endoscope according to claim 1, wherein the distal end portion includes:

an image pickup window, and a third channel including a third opening disposed outside of the recess, wherein the third channel is configured to discharge a second liquid toward the image pickup window via the third opening.

3. The endoscope according to claim 2, wherein the first liquid and the second liquid are supplied from a common reservoir.

4. The endoscope according to claim 1, wherein a discharge area of the first liquid covers an outer diameter of the treatment instrument disposed at the raising base.

5. The endoscope according to claim 1, wherein the proximal portion of the second channel extends in a second direction, and wherein the second direction is parallel to the first direction.

6. The endoscope according to claim 1, wherein the inner surface forming the recess includes:

a proximal surface, a distal surface, and a plurality of side surfaces connecting the proximal surface to the distal surface, and wherein the first opening is in the proximal surface.

7. The endoscope according to claim 6, wherein the second opening is in the proximal surface.

8. The endoscope according to claim 7, further comprising a third channel including a third opening, wherein the third opening is in one of the plurality of side surfaces.

9. The endoscope according to claim 8, wherein the distal end portion includes an image pickup window, and wherein the third channel is configured to discharge a second liquid toward the image pickup window via the third opening.

10. The endoscope according to claim 8, wherein the discharge axis intersects the raising base in the upright state.

11. The endoscope according to claim 6, wherein the second opening is in one of the plurality of side surfaces.

12. The endoscope according to claim 11, wherein the second channel further includes a third opening, and wherein the third opening is in one of the plurality of side surfaces.

13. The endoscope according to claim 11, wherein the discharge direction of the first liquid is toward a bottom surface.

14. The endoscope according to claim 1, wherein the first liquid discharged from the second channel via the second opening is a first liquid portion, wherein the second channel further includes a third opening disposed at the inner surface and the second channel is further configured to discharge a second liquid portion to inside of the recess via the third opening, and wherein the first liquid portion is directed toward the raising base and the second liquid portion is directed toward the raising base.

15. The endoscope according to claim 14, wherein the first liquid portion is directed toward a first portion of the raising base and the second liquid portion is directed toward a second portion of the raising base, where the first portion of the raising base is different from the second portion of the raising base.

16. An endoscope system, comprising the endoscope according to claim 1.

17. The endoscope system according to claim 16, further comprising a liquid feed device configured to supply the first liquid to the second channel.

18. The endoscope system according to claim 16, further comprising:

a treatment instrument in the first channel, wherein the treatment instrument is translatable in the first channel to project from the first opening in a projecting direction, and wherein the raising base is operable to change the projecting direction of the treatment instrument.

19. The endoscope according to claim 1, wherein the raising base is operable to move between a laid state and an upright state, and wherein the discharge axis intersects the raising base in the laid state.

* * * * *